(12) United States Patent
Ishii

(10) Patent No.: US 9,222,180 B2
(45) Date of Patent: Dec. 29, 2015

(54) DEODORIZATION AND STERILIZATION APPARATUS

(71) Applicant: Yoshihisa Ishii, Saitama (JP)

(72) Inventor: Yoshihisa Ishii, Saitama (JP)

(*) Notice: Subject to any disclaimer, the term of this patent is extended or adjusted under 35 U.S.C. 154(b) by 157 days.

(21) Appl. No.: 14/164,923

(22) Filed: Jan. 27, 2014

(65) Prior Publication Data

US 2014/0209454 A1 Jul. 31, 2014

(30) Foreign Application Priority Data

Jan. 28, 2013 (JP) ................ 2013-012730

(51) Int. Cl.
*C25B 1/26* (2006.01)
*C25B 9/08* (2006.01)
*C25B 15/02* (2006.01)
*A01N 59/00* (2006.01)
*A61L 9/12* (2006.01)

(52) U.S. Cl.
CPC . *C25B 1/26* (2013.01); *A01N 59/00* (2013.01); *C25B 9/08* (2013.01); *C25B 15/02* (2013.01); *A61L 9/12* (2013.01); *A61L 2209/213* (2013.01)

(58) Field of Classification Search
CPC .............. C25B 1/26; C25B 9/08; C25B 15/02
USPC ............................................ 204/229.5, 229.6
See application file for complete search history.

(56) References Cited

U.S. PATENT DOCUMENTS

| 2010/0078331 A1* | 4/2010 | Scherson | .................. C25B 1/24 205/335 |
| 2012/0085658 A1* | 4/2012 | Bhavaraju | ................. C25B 1/10 205/443 |
| 2014/0124377 A1* | 5/2014 | Joynt | .................... C02F 1/4674 205/335 |

FOREIGN PATENT DOCUMENTS

| JP | 2002349913 A | 12/2002 | |
| JP | 3154192 U | 8/2009 | |
| JP | 2012196643 A | * 10/2012 | ................ C25B 9/00 |

* cited by examiner

*Primary Examiner* — Nicholas A Smith
(74) *Attorney, Agent, or Firm* — Venable LLP; Henry J. Daley

(57) ABSTRACT

A safe and low cost deodorization and sterilization apparatus is provided for continuously deodorizing in a restroom, around a garbage box, in an indoor room and the like for a long period of time, utilizing a deodorization power of a hypochlorous acid, not requiring frequent supplement of water. The deodorization and sterilization apparatus is adapted to control a electric current value ratio or a electric current amount ratio of an electrode with a diaphragm (a salt path with ion conductivity and very slight flow of water) and an electrode without diaphragm or to control a positive/negative electric current amount of the electrodes in electrolysis of an aqueous chloride salt solution, so that a PH value and the hypochlorous acid concentration are adjusted, thereby evaporating and diffusing the generated hypochlorous acid for deodorization and sterilization.

8 Claims, 5 Drawing Sheets

DEODORIZATION AND STERILIZATION APPARATUS

CROSS REFERENCE TO RELATED APPLICATION

The present application claims priority under the Paris Convention to Japan Patent Application No. 2013-012730, filed on Jan. 28, 2013. The entire content of such prior application is incorporated herein by reference.

TECHNICAL FIELD

The present invention pertains to a deodorization and sterilization apparatus to be used for deodorization in a restroom, around a garbage box, and in an indoor room, the deodorization and sterilization apparatus being adapted to electrolyze an aqueous chloride salt solution of salt or the like to generate hypochlorous acid and then evaporate the generated hypochlorous acid, to perform deodorization and sterilization by utilizing oxidizability of the hypochlorous acid.

BACKGROUND ART

Up until now, there have been various kinds of aromatic deodorant used for deodorization in a restroom, around a garbage box, and in an indoor room. Further, in places where residual aromatic odor is disliked, there have so far been active charcoal, zeolite and the like used for deodorization of the residual aromatic odor by adsorbing the residual aromatic odor. Furthermore, conventionally, there have so far been used various deodorization methods for deodorizing odors by utilizing a strong oxidizability of the hypochlorous acid: to electrolyze an aqueous chloride salt solution of salt or the like to generate the hypochlorous acid and then spray the generated hypochlorous acid by a spraying device or evaporate the generated hypochlorous acid by an evaporating material.

There is known a deodorization and sterilization apparatus adapted to fill a vessel with a hypochlorous acid solution, to have an evaporation promotion material impregnated with the hypochlorous acid solution, and then to blow a wind by a fan against the evaporation promotion material impregnated with the hypochlorous acid solution, thereby evaporating the hypochlorous acid solution (See Patent Document 1). There is also known a deodorization and sterilization apparatus adapted to put the hypochlorous acid solution in an ultrasonic humidifier and then to spray the hypochlorous acid solution (See Patent Document 2).

CITATION LIST

Patent Literature

Patent Document 1: Japanese Patent Application Publication No. 2002-349913
Patent Document 2: Japanese Registered Utility Model Publication No. 3154192

SUMMARY OF INVENTION

Technical Problem

The inventions disclosed in the above listed patent documents are originally aimed to humidify indoor rooms, so that the conventional deodorization and sterilization apparatuses disclosed in the above listed patent documents must be frequently supplied with water in order to spray or evaporate a large quantity of water. The conventional deodorization and sterilization apparatuses experience troubles in spraying the large quantity of water when humidification is not required. Further, the conventional deodorization and sterilization apparatuses store large quantity of hypochlorous acid solution, so that the conventional apparatuses are large in size. Furthermore, the conventional deodorization and sterilization apparatuses are provided with a fan and an evaporation promotion material therein, so that the conventional apparatuses are large and complicated in structure. In the conventional deodorization and sterilization apparatuses provided therein with a hypochlorous acid generation device including a diaphragm, a PH value of a generated liquid is low and consequently chlorine generated as a result of electrolyzation is directly released into the atmosphere, so that the hypochlorous acid generation device cannot be used in presence of people. Accordingly, in the conventional deodorization and sterilization apparatuses, the hypochlorous acid solution generated in another place is moved into a spraying device which sprays the hypochlorous acid solution, thereby making it necessary to frequently supplement the liquid. Still further, in the deodorization and sterilization apparatuses provided therein with the hypochlorous acid generation device without the diaphragm, the generated liquid turns alkaline, so that the hypochlorous acid turns into hypochlorite of soda, thereby making it impossible to continuously evaporate the hypochlorous acid.

The present invention has been made to overcome the previously mentioned conventional problems, and therefore an object of the present invention lies in providing a deodorization and sterilization apparatus that controls the PH value of the generated liquid and a concentration of the hypochlorous acid and evaporates the hypochlorous acid, the deodorization and sterilization apparatus generating no chlorine gas, being usable in presence of people, safe, compact in size, simple in structure, low cost, and not requiring frequent supplement of the liquid.

Solution to Problem

The first aspect of present invention is a deodorization and sterilization apparatus that electrolyzes an aqueous chloride salt solution filled in a vessel to generate a hypochlorous acid, the deodorization and sterilization apparatus comprising: a tank A having an opening formed therein and having a negative electrode (hereinafter, "negative electrode" refers to an electrode which electric current amount as a positive pole is equal to or smaller than a half of the total electric current amount at the electrode) and a positive electrode (hereinafter, "positive electrode" refers to an electrode which electric current amount as a positive pole is equal to or larger than a half of the total electric current amount at the electrode) provided therein, the opening communicating with an outside air; a tank B having an opening or a clearance formed therein and having a negative electrode provided therein, the opening or the clearance communicating with an outside air; a salt path (hereinafter, "salt path" refers to an electric current path including a diaphragm, the electric current path having ion conductivity by solute however having small liquid flow, the electric current path being prepared by having an aqueous solution of salt infiltrated into a fiber, filled into a narrow tube, fixed by a gel-like material or the like) that electrically connects the aqueous chloride salt solution in the tank A and the aqueous chloride salt solution in the tank B with each other; a direct current power unit that electrifies the positive electrode and the negative electrode; and a control unit that controls a ratio of an electric current value or an electric current quantity of an electric current in the negative electrode in the tank A and an electric current in the negative electrode in the tank B.

The second aspect of the present invention is a deodorization and sterilization apparatus that electrolyzes an aqueous chloride salt solution filled in a vessel to generate a hypochlorous acid, the deodorization and sterilization apparatus comprising: a tank A having an opening formed therein and having a positive electrode provided therein and optionally having a negative electrode provided therein, the opening communicating with an outside air; a tank B having an opening or a clearance formed therein and having a negative electrode provided therein, and optionally having a positive electrode provided therein, the opening or the clearance communicating with an outside air; a salt path that electrically connects the aqueous chloride salt solution in the tank A and the aqueous chloride salt solution in the tank B with each other; a direct current power unit that electrifies the positive electrode and the negative electrode; and a reverse and control unit that reverses a polarity of the electrode in the tank A and a polarity of the electrode in the tank B and controls a ratio of positive-reverse electrified time or a ratio of positive-reverse electric current quantity.

The third aspect of the present invention is a deodorization and sterilization apparatus in which the salt path is constituted by a retention material or a salt bridge, the retention material being a material that retains the aqueous chloride salt solution by a non-woven textile fabric or a felt-like suction material. The fourth aspect of the present invention is a deodorization and sterilization apparatus, in which the positive electrode and optionally the negative electrode are accommodated in a hollow member having openings respectively in an upper portion and a lower portion thereof, the upper portion of the hollow member being communicated with the outside air through a gas transparent member which has a gas transparency. The fifth aspect of the present invention is a deodorization and sterilization apparatus, in which the gas transparent member is constituted by a gas transparent material or a clearance forming member that forms a clearance between the clearance forming member and the hollow member.

Advantageous Effects of Invention

The present invention has advantageous effects as explained hereinafter. The deodorization and sterilization apparatus according to the present invention can (1) adjust an electric current value, an electric current quantity or a ratio thereof in an negative electrode of a tank A and an negative electrode of a tank B, or (2) adjust a positive-negative ratio by repeatedly reversing a polarity of the tank A and a polarity of the tank B, thereby making it possible to adjust the quantity of the hypochlorous acid and a PH value of the hypochlorous acid solution generated in the tank A. The chlorine generated by electrolyzing chlorine ion included in $CL_2$, HClO or ClO- ion is in an equilibrium state. However, it is possible to control a quantity of the hypochlorous acid necessary for deodorization and a quantity of evaporation of chlorine which is harmful for human being and things by adjusting the quantity of the hypochlorous acid and the PH value. The hypochlorous acid is diffused into an outside air through an opening portion of the tank A to react with an odor component in the outside air for deodorization, while alkaline in the tank B absorbs a carbon dioxide from the outside air through an opening portion of the tank B, so that the aqueous solution in the tank B is neutralized, thereby making it possible to reduce the quantity of the alkaline in the tank B to a level smaller than a level that is harmful for human skin. Further, the deodorization and sterilization apparatus according to the present invention can increase an evaporation ratio of the hypochlorous acid and water in comparison with conventional evaporation devices having provided therein with a supersonic splaying device or an evaporation promotion material, so that a water reduction amount is largely reduced, thereby making it possible to largely extend a water supplement time interval. The electric current to be employed is approximately 1 mA in most cases, so that the deodorization and sterilization apparatus according to the present invention can be operated for three to five months by a size D battery. Furthermore, a deliquescent hypochlorous acid solution, such as a high concentration calcium chloride, can be used, so that a moisture component is absorbed from the outside air, thereby making it possible to continuously use the deodorization and sterilization apparatus for a long period of time without supplementing water. By this structure, it is possible to provide a low-cost, compact-size and simple-structure deodorization and sterilization apparatus which does not perform unnecessary humidification and drastically reduces a frequency of required liquid supplement.

By the construction as set forth in the above definition, the deodorization and sterilization apparatus according to the present invention can easily and safely generate and evaporate the hypochlorous acid for deodorization and sterilization of a restroom, a garbage and an indoor room.

DESCRIPTION OF EMBODIMENTS

Figure 1:
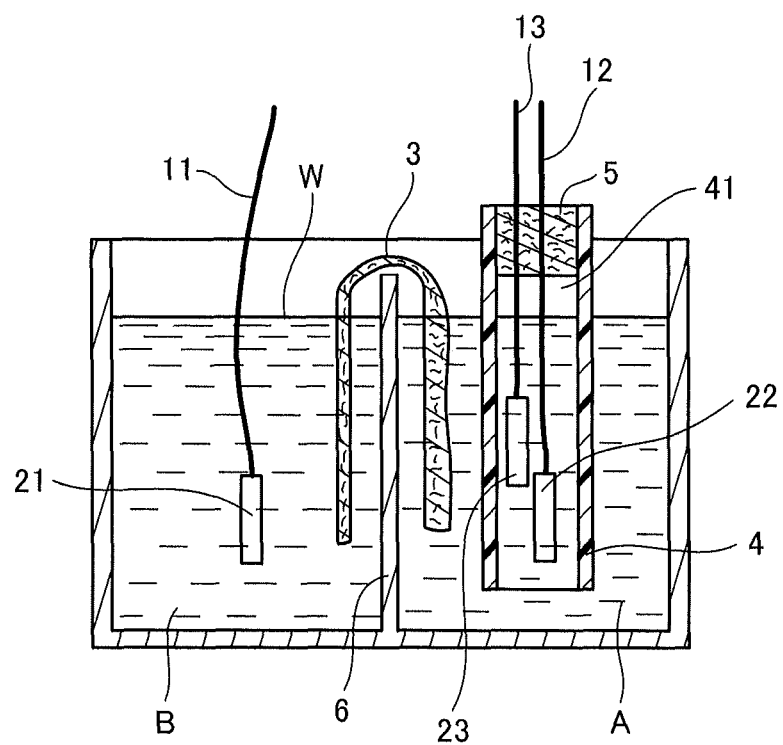
FIG. 1 is a schematic cross sectional view of the deodorization and sterilization apparatus according to the first embodiment of the present invention.

Next, the first embodiment of the present invention will be explained hereinafter in detail with reference to FIG. 1. A tank A and a tank B are filled with an aqueous chloride salt solution such as salt water. A vessel is divided into two tanks A and B by a partition plate 6. A salt path 3 is constituted by a suction material rolling over the partition plate 6 and extending to beneath a liquid surface of the tank A and the tank B. The tank A is provided therein with a positive electrode 22 connected with a positive electrode lead cable 12 and a negative electrode 23 connected with a negative electrode lead cable 13, while the tank B is provided therein with a negative electrode 21 connected with a negative electrode lead cable 11. The positive electrode lead cable 12 is applied with a plus potential and the negative electrode lead cables 13 and 23 are applied with a minus potential by a current control device not shown having a plurality of means to control a current value using a known current diode, a known constant current circuit and the like, so that each of the electrodes is respectively applied with a predetermined electrolytic current, thereby generating the hypochlorous acid in the tank A. A diaphragm-free electrolysis wherein the electrolytic current flows in the positive electrode lead cable 12 and the negative electrode lead cable 13 generates sodium hypochlorite, so that a liquid in the tank A is alkalinized, while a salt-path electrolysis (hereinafter, "salt-path electrolysis" refers to an electrolysis wherein the negative electrode and the positive electrode are connected with each other through the salt path) wherein the electrolytic current flows in the positive electrode lead cable 12 and the negative electrode lead cable 11 generates hydrochloric acid and hypochlorous acid, so that the liquid in the tank A is acidified. The deodorization and sterilization apparatus according to the present invention adjusts a current value ratio of the diaphragm-free electrolysis and the salt-path electrolysis, so that a PH value of the aqueous solution is adjusted, thereby obtaining the aqueous solution abundantly inclusive of the hypochlorous acid without evaporation of chlorine included therein. The hypochlorous acid thus generated is evaporated to be diffused into an outside air through an opening portion of the tank A, so that the hypochlorous acid reacts with an odor component in the outside air, thereby deodorizing the outside air. W shows a water level of the aqueous chloride salt solution. In this embodiment, the positive electrode and the negative electrode are constituted by a titan coated and sintered with substrate iridium oxide. However, the positive electrode and the negative electrode may otherwise be constituted by any other insoluble electrode having a low chlorine overvoltage. The negative electrode may be constituted by an insoluble electrode with no particular restriction and may be constituted by a material same as the material of the positive electrode or an insoluble electrode made of a platinum or the like. The lead cables may be constituted by an insoluble material such as titanium covered and insulated by a heat-shrinkable tube. However, the lead cables may otherwise be constituted by a cupper cable provided that the lead cables are covered with a sufficiently insulating material. In the present embodiment of the deodorization and sterilization apparatus, a single positive electrode is shared. However, the present invention is not limited to this construction, and the deodorization and sterilization apparatus according to the present invention may be constituted to have two positive electrodes by dividing the single positive electrode into two positive electrodes, one of which may be disposed in the tank B to be used for adjusting the PH value with the electric current ratio or the like. A hollow member 4 is a hollow body having opening portions respectively in an upper portion and a lower portion thereof, the hollow member 4 being particularly used when an evaporation of chlorine and diffusion of chlorine gas are desired to be suppressed. The positive electrode 22 is arranged in the lower portion of the hollow member 4, while the negative electrode 23 is arranged above the positive electrode 22, and a gas transparent member 5 is pushed into the upper portion of the hollow member 4 in a semi-sealed state. Between the electrode 23 and the gas transparent member 5 is a space, and the hollow member 4 is submerged to a height position that the space is not filled with the aqueous chloride salt solution. In response to application of plus potential to the positive electrode lead cable 12 and minus potential to the negative electrode lead cables 11, 13 from a direct current source not shown, there are generated hydrogen gas at the negative electrode 21, 23, and oxygen gas and chlorine gas at the positive electrode 22 as a result of an electrolysis, wherein a part of the chlorine drawn into bubbles of the oxygen gas and the hydrogen gas to be elevated and released into a hollow member inner upper space 41. The chlorine gas thus released into the hollow member inner upper space 41 is prevented from being directly released into the outside air by existence of the gas transparent member 5, so that the chlorine gas in touch with the aqueous solution is gradually dissolved into the aqueous solution, thereby causing the chlorine gas to be rarified. The chlorine gas thus rarified little by little penetrates through the gas transparent member 5 to be released into the outside air together with the oxygen gas and the hydrogen gas. Positions of the positive electrode 22 and the negative electrode 23 are not limited to the positions as described above. However, positioning the negative electrode 23 above the positive electrode 22 as explained above causes an upper portion the aqueous solution more alkalinized, so that absorption of the chlorine gas in the hollow member inner upper space 41 is enhanced, thereby causing the chlorine gas more ratified. The hollow member inner upper space 41 is not necessarily indispensable, however without the hollow member inner upper space 41, the gas transparent member 5 is clogged by absorption of water and adhesion of scale component in lapse of usage time, so that gas transparency becomes instable. The hypochlorous acid generated in the hollow member 4 is diffused from a lower opening of the hollow member 4 into the entire tank A to be evaporated on a gas-liquid interface into the outside air. A material of the hollow member 4 can be but not limited to a general-purpose material such as polyethylene resin, polypropylene resin, polyester resin, ABS resin, vinyl chloride resin or the like. The gas transparent member 5 may be constituted by a material that can gradually and slightly allow the gas to be penetrated through, such as a compressed non-woven textile fabric, a compressed felt-like suction material, a material utilizing gas transparency of a hollow fiber diaphragm, a material having a shape forming a slight space from four inner surfaces of the hollow member 4, or the like. Size of the hollow member 4 needs to be appropriately determined depending on a required current value and adjusted PH value. The hollow member 4 can be omitted for example in a case that the deodorization and sterilization apparatus according to the present invention is used in a place where there is no harm to persons or items around. A material of the tanks A, B can be but not limited to a general-purpose material such as polyethylene resin, polypropylene resin, polyester resin, ABS resin, vinyl chloride resin or the like. A material of the salt path 3 can be but not limited to a non-woven textile fabric or a felt-like polyester having wettability and low cost. The tank A and the tank B can be electrically connected by providing a diaphragm such as an ion exchange diaphragm in a portion of the partition plate 6 below water surface. Further, a salt bridge may by prepared by solidifying the aqueous chloride salt solution into a gel state. Since the tank A and the tank B are connected with each other through the salt path 3, there is little exchange of water between the tank A and the tank B, so that the soluble fraction in the tank A and in the tank B are rarely not mixed. A hypochlorous acid can be evaporated from the hypochlorous acid solution by a natural evaporation from a water surface with no external force. However, an evaporation quantity of the hypochlorous acid can be increased by extending a launch area of an evaporation material or by a forced evaporation such as, air blasting or bubbling. In the deodorization and sterilization apparatus in the present invention, water is evaporated along with the hypochlorous acid, so that supplementation of water is required. However, a longer time operation is possible for example by providing with a cartridge tank. In the deodorization and sterilization apparatus in the present invention, the tank A and tank B are formed by partitioning on vessel into two portions by the partition plate 6. However, the tank A and the tank B can be separately constituted respectively by a vessel.

Next, the second embodiment of the present invention will be explained with reference to FIG. 2, with particular focus on differing points from the first embodiment associated with FIG. 1. In the present embodiment PH value adjustment is performed by polarity inversion of the electrode, while in the first embodiment PH value adjustment is performed by controlling current value and current value ratio in the diaphragm-free electrolysis and in the salt-path electrolysis. In the present embodiment, the tank A is provided therein with the positive electrode 22, which is unsolvable and used for electrolysis, connected with an electrode lead cable 12, while the tank B is provided therein with the negative electrode 21, which is unsolvable and used for electrolysis, connected with an electrode lead cable 11, wherein a repeatedly inverted electrolysis current is applied into the electrode lead cables 11, 12 from a current control device not shown, so that the hypochlorous acid is generated. The hollow member 4 is provided and used in a similar way as in the first embodiment, for example when the deodorization and sterilization apparatus is used in a place where the evaporation of chlorine gas is harmful to persons or items around. When the evaporation of chlorine gas is especially undesirable in a case that the electrolysis is performed with repeated inversion of electric current direction, it is desirable to have the hollow member 4 in the tank A provided with two electrodes, one electrode being used only when the tank A is positively charged while the other electrode being used when the tank A is negatively charged, the other electrode for negative charge being arranged upward of the on electrode for positive charge, and to have the hollow member 4 in the tank B arranged in a similar way.

Next, a PH value condition to be satisfied for the evaporation of the hypochlorous acid from the aqueous solution into the atmosphere will be explained hereinafter. A part of the chlorine generated in the tank A by the electrolysis of chlorine ion reacts with water around to generate hydrochloric acid and hypochlorous acid, however in case of the salt-path electrolysis, the PH value of the aqueous solution is low, so that a large part of the generated chlorine remains as chlorine in the water, with the result that the chlorine remained in the water is diffused into the atmosphere which is in partition equilibrium with the chlorine remained in the water. Further, in case of the diaphragm-free electrolysis, the aqueous solution turns alkaline, so that concentration of the hypochlorous acid in the aqueous solution is decreased, with the result that the generated chlorine cannot be evaporated. Accordingly, the PH value adjustment of the aqueous solution is indispensable.

A relationship between the concentration of the chlorine remained in the aqueous solution and the concentration of the chlorine gas in the atmosphere in the neighborhood of the gas-liquid interface in equilibrium with the chlorine remained in the water can be obtained as explained hereinafter. The chlorine generated by the electrolysis reacts with the water, so that the hydrochloric acid and the hypochlorous acid.

$$Cl_2 + H_2O \rightarrow HCl + HClO$$

$$K_{cl2} = [HCl] \times [HClO]/[CL2] = 1.56 \times 10^{-4}$$

The generated hypochlorous acid is diverged into hydrogen ion and hypochlorous acid ion.

$$HClO \rightarrow H^+ + ClO^-$$

$$K_{hcol} = [H^+] \times [ClO^-]/[HClO] = 10^{-7.53}$$

Here, "$K_{cl2}$" and "$K_{hclo}$" denote an equilibrium constant of respective reaction formulas. Provided that the chlorine gas solved in the aqueous solution conforms to the law of Henry, chlorine gas concentration of the atmosphere in equilibrium with the aqueous solution can be obtained by the reaction formulas as shown below, where $P_{Cl2}$ denotes the chlorine gas concentration of the atmosphere in equilibrium with the aqueous solution in unit of parts per million (hereinafter simply referred to as "ppm"), "$[CL_2]$" denotes the chlorine concentration in the aqueous solution, "$CL_2$" denotes the residual chlorine concentration in the aqueous solution in unit of mg/l, "h" denotes the Henry constant and the Henry constant h employs the value by AIETA E M, ROBERTS P V (Stanford Univ., California).

$$P_{cl2} = h \times [Cl_2]$$

$$P_{cl2} = h \times CL_2 \times 2.54 \times 10^{-7}/(1 + 1.56 \times 10^{-4+PH})$$

$$h = 13.57 \text{ atmx (l/mol)} = 1.911 \times 10^8 \text{ ppm/(mg/l)} \quad (1)$$

Generally, a value of the chlorine concentration in the air, that a person feels no discomfort in throat, bronchus and lung after staying for a long time in a room in which the chlorine is generated, largely varies from person to person. However, there has been no person who appealed a discomfort in cases that the value of the chlorine concentration obtained by the above formula (1) is 0.001 ppm or less.

TABLE 1

| | | | | | | | | | | | | |
|---|---|---|---|---|---|---|---|---|---|---|---|---|
| | | | | | | Influence of current value variation | | | | | | |
| Test Apparatus No. | Test No. | Salt-Path Electrolysis Current mA | Diaphragm-free Electrolysis Current mA | Current Value *1 mA | Current Value Ratio Positive/Toal | Water Quantity ml | PH value (CLO side) | PH value (OH side) | Tank A CLO mg/l | Opening Portion Chlorine Odor/Stimulus | Restroom Odor | Garbage Odor |
| T5 | 1 | 0 | 1.23 | 1.23 | 0.5 | 331 | 8.2 | | 1140 | None/None | X | X |
| T5 | 2 | 0.74 | 1.09 | 1.82 | 0.627 | 331 | 8.0 | 9.2 | 1390 | None/None | ○ | ○ |
| T2 | 3 | 0.26 | 0.78 | 1.02 | 0.571 | 331 | 7.5 | 8.9 | 1110 | None/None | | |
| T2 | 4 | 0.25 | 0.75 | 0.97 | 0.571 | 331 | 8.0 | 8.9 | 1330 | None/None | | |

TABLE 1-continued

Influence of current value variation

| Test Apparatus No. | Test No. | Salt-Path Electrolysis Current mA | Diaphragm-free Electrolysis Current mA | Current Value *1 mA | Current Value Ratio Positive/Total | Water Quantity ml | PH value (CLO side) | PH value (OH side) | Tank A CLO mg/l | Opening Portion Chlorine Odor/Stimulus | Restroom Odor | Garbage Odor |
|---|---|---|---|---|---|---|---|---|---|---|---|---|
| T2 | 5 | 0.25 | 0.75 | 0.97 | 0.571 | 331 | 8.0 | 8.9 | 1390 | None/None | ○ | ○ |
| T2 | 6 | 0.25 | 0.75 | 0.97 | 0.571 | 331 | 8.1 | 8.9 | 940 | None/None | | |
| T2 | 7 | 0.25 | 1.56 | 1.81 | 0.537 | 331 | 7.5 | 9.2 | 1790 | None/None | | |
| T4 | 8 | 0.07 | 0.6 | 0.65 | 0.528 | 242 | 6.9 | 10.3 | 75 | None/None | ○ | ○ |
| T4 | 9 | 0.62 | 1 | 1.61 | 0.618 | 242 | 6.9 | 10.3 | 75 | None/None | | |
| T4 | 10 | 0.62 | 1 | 1.61 | 0.618 | 242 | 6.7 | 10.3 | 124 | None/None | | |
| T4 | 11 | 0.62 | 1 | 1.61 | 0.618 | 242 | 7.3 | 10.3 | 330 | None/None | ○ | ○ |
| T4 | 12 | 0.62 | 1 | 1.61 | 0.618 | 242 | 7.3 | 10.3 | 335 | None/None | ○ | |
| T4 | 13 | 0.62 | 1 | 1.61 | 0.618 | 242 | 7.4 | 9.4 | 300 | None/None | ○ | ○ |
| T8 | 14 | 0.48 | 1.19 | 1.67 | 0.584 | 990 | 3.9 | 9.8 | 10 | None/None | ○ | |
| T8 | 15 | 0.48 | 1 | 1.67 | 0.597 | 990 | 5.9 | 9.7 | 22 | None/None | ○ | |
| T8 | 16 | 0.48 | 1 | 1.67 | 0.597 | 990 | 6.7 | 9.6 | 156 | None/None | ○ | |
| T8 | 17 | 0.48 | 1 | 1.67 | 0.597 | 990 | 6.9 | 9.3 | 92 | None/None | ○ | |
| T8 | 18 | 0.48 | 1 | 1.67 | 0.597 | 990 | 6.8 | 9.3 | 108 | None/None | ○ | ○ |
| T8 | 19 | 0.48 | 1 | 1.67 | 0.597 | 990 | 6.8 | 9.3 | 91 | | | |
| T9 | 20 | 0.62 | 1 | 1.61 | 0.618 | 100 | 7.8 | 10.3 | 235 | None/None | ○ | ○ |
| T9 | 21 | 0.59 | 0.98 | 1.56 | 0.616 | 100 | 8.0 | 9.8 | 313 | None/None | & | ○ |
| T10 | 22 | 0.62 | 0 | 0.62 | 1 | 315 | 2.0 | 9.9 | 0.2 | CL2 Odor ? | | |
| T11 | 23 | 1.03 | 0 | 1.03 | 1 | 315 | 4.6 | 11.0 | 17 | CL2 Odor ? | | |

Current Value *1: May differ from a sum of separately measured values, because positive polar is shared.
Current Value Ratio: Tank A Positive Polar Current Value/(Tank A Positive Polar Current Value + Tank A Negative Polar Current Value)
CLO: Residual Chlorine
○: No odor confirmed.
&: Slight odor
X: Unable to deodorize
CL2 Odor ?: Extremely slight odor. A person feels discomfort in throat, bronchus and lung after staying for a long time in a room.
Blank cell in the table denotes no measurement .

Table 1 shows results of an experiment using an apparatus as shown in FIG. 1, wherein the positive electrode 22 in the tank A is connected to a plus terminal of a battery or a direct current source not shown, a plurality of constant current diodes (constant current diodes with varying constant current values are exchanged as necessary) connected to a minus terminal of the battery or the direct current source are respectively connected to the negative electrode 21 in the tank A and the negative electrode 23 in the tank B, an electrolysis current of approximately 1 mA is applied respectively to the negative electrode 21 in the tank A and the negative electrode 23 in the tank B, varied a current value ratio, and placed the apparatus in a restroom and around a garbage box. The PH value was measured by B-211 manufactured by HORIBA, Ltd., the residual chlorine was measured by AQ-102 manufactured by SIBATA SCIENTIFIC TECHNOLOGY LTD., and the $CL_2$ odor was confirmed by the olfactory sense of human being. To be more specific, the restroom odor confirmed include odor at defecation time and odor adhered to around a toilet, and the garbage odor confirmed include odor leaked out of the garbage box and odor generated by opening and closing the rid of the garbage box. In confirmation of the restroom odor, the atmospheric temperature was not taken into account for the defecation temperature is constant, while in the garbage odor confirmation, the vicinity of the garbage box was maintained between 18° C.-25° C. Hereinafter, the same measurement devices and the same measurement methods are applied. Based on the result of Test No. 1, the restroom odor and the garbage odor cannot be deodorized by the diaphragm-free electrolysis alone. Meanwhile, based on the results of Test No. 10 and 11, in cases of the salt-path electrolysis alone or in cases of the PH value being 5 or less, a person may feel a discomfort of light cold symptom in throat, bronchus or lung after staying for a long time in a room in which the chlorine is generated. Accordingly, the apparatus with the salt-path electrolysis alone or the PH value being 5 or less is not desirably used in constant presence of people. The PH value may desirably be between 5 and 8, and more desirably be between 6.5 and 7.8. The electric current value ratio or the electric current amount ratio of the negative electrode 23 in the tank A and the negative electrode 21 in the tank B, wherein the PH value of the tank A and the PH value in the tank B are within a desirable range, vary depending on water quality, metal ion amount and carbonic acid ion amount of sewage water to be used. Therefore, the or the electric current amount ratio of the negative electrode 23 in the tank A and the negative electrode 21 in the tank B need to be appropriately set in a condition wherein the apparatus is used. Variation of the electrolysis electric current value varies the PH value and the hypochlorous acid concentration of the aqueous solution. The electric current value ratio and the like are desirably set in consideration of the hypochlorous acid concentration in the tank A, the PH value in the tank B as well as the hypochlorous concentration to be set to 1,000 mg/l or less and the PH value to be set to 11.4 or less so that skin is not damaged even when dipped into the aqueous solution. For deodorization of the odor in the restroom and around the garbage box, sufficient amount of the hypochlorous acid can be obtained by applying approximately 1 mA electrolysis current in a case of the aqueous solution being a 3% salt water. An electrolysis efficiency of the positive electrode 22 employed in the present embodiment is approximately 20 mg/mA Day of HClO in a case of an aqueous solution of 3% or more salt, approximately 15 mg/mA Day of HClO in a case of an aqueous solution of 2% salt and approximately 8 mg/mA Day of HClO in a case of an aqueous solution of 1% salt. Although the concentration of chloride salt is not limited, the salt concentration of the aqueous solution is desirably 2.5% or more.

TABLE 2

| Test Apparatus No. | Test No. | Positive Polar min. | Negative Polar min. | Current mA | Current Ratio | Water Quantity ml | Tank A PH value | Tank B PH value | Tank A CLO mg/l | Opening Portion Chlorine Odor/ | Restroom Odor | Garbage Odor |
|---|---|---|---|---|---|---|---|---|---|---|---|---|
| T13 | 1 | 30 | 30 | 1.93 | 0.5 | 367 | 8.2 |  | 1100 | None/None | X | X |
| T14 | 2 | 30 | 25 | 2.32 | 0.545 | 242 | 7.8 | 9.1 | 635 | None/None | ○ | ○ |
| T10 | 3 | 30 | 20 | 2.35 | 0.6 | 360 | 7.3 | 9.4 | 435 | None/None | ○ | ○ |
| T11 | 4 | 30 | 15 | 1.92 | 0.667 | 228 | 3.9 | 10.3 | 102 | CL2 Odor ? | ○ | ○ |
| T15 | 5 | 30 | 10 | 2.15 | 0.75 | 242 | 3.6 | 10.1 | 93 | CL2 Odor ? | ○ | ○ |
| T12 | 6 | 30 | 5 | 2.25 | 0.857 | 315 | 2.9 | 11.4 | 62 | CL2 Odor ? | ○ | ○ |
| T3 | 7 | 30 | 0 | 0.62 | 1 | 315 | 2.8 | 9.9 | 47 | CL2 Odor ? | ○ | ○ |

Current Ratio: Positive Polar Current Quantity/(Positive Polar Current Quantity + Negative Polar Current Quantity)
CLO: Residual Chlorine
○: No odor confirmed.
&: Slight odor
CL2 Odor ?: Extremely slight odor. A person feels discomfort in throat, bronchus and lung after staying for a long time in a room
X: Unable to deodorize
Blank cell in the table denotes no measurement.

Figure 2:
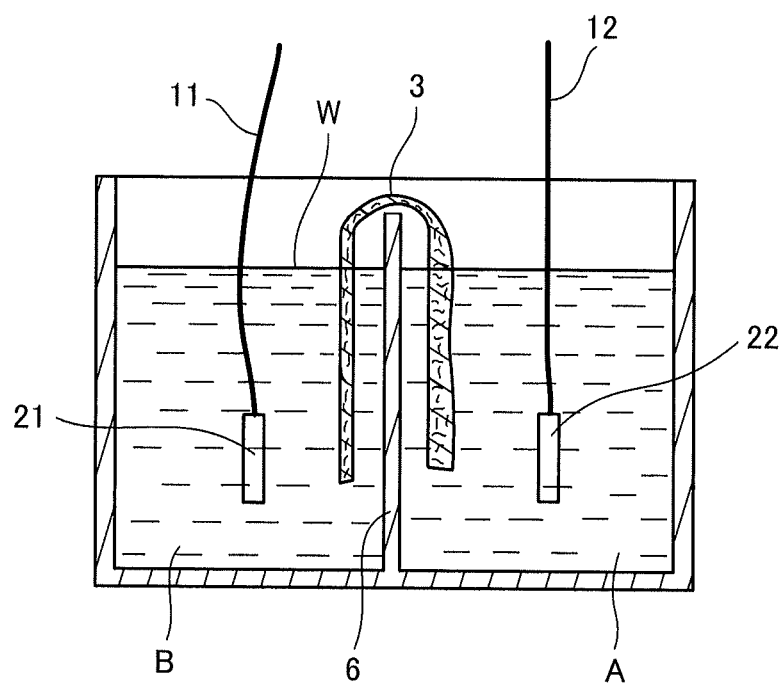
FIG. 2 is a schematic cross sectional view of the deodorization and sterilization apparatus according to the second embodiment of the present invention.

Table 2 shows measurement results of the PH value, the hypochlorous acid and the like in the tank A and the tank B, using an apparatus as shown in FIG. 2, wherein a combination of a constant current diode not shown connected to a power source and a timer not shown is used to have the positive electrode 22 in the tank A and the negative electrode 21 in the tank B applied with approximately 1 mA of electrolysis current, so that an aqueous solution in the tank A and an aqueous solution in the tank B are electrolyzed with a polarity being repeatedly inverted. To be more specific, a forward current and a reverse current are repeatedly inverted to each other for a long time until the PH value in the tank A and the residual chlorine in the tank became constant, in such a manner that the positive electrode 22 in the tank A is electrified for 30 minutes by an electrolysis current (a forward current) and thereafter the negative electrode 21 in the tank B is electrified an electrolysis current (a reverse current) for 5 to 25 minutes. Then, the PH value in the tank A, the residual chlorine, $Cl_2$ odor and PH in the tank B were measured at the time when the PH value in the tank A and the residual chlorine in the tank thus became constant. The PH value was measured by B-211 manufactured by HORIBA, Ltd., the residual chlorine was measured by AQ-102 manufactured by SIBATA SCIENTIFIC TECHNOLOGY LTD., and the $CL_2$ odor was confirmed by the olfactory sense of human being. In Table 2, a positive polarity min column denotes a time in unit of minutes during which the tank A polarity is held positive, while a negative polarity min column denotes a time in unit of minutes during which the tank A polarity is held negative. In Table 2, electric current ratio denotes a value obtained by dividing a positive polarity current amount by a sum of the positive polarity current amount and a negative polarity amount, the positive polarity current amount being a product of a time (minutes) during which the tank A polarity is held positive and the electric current value (mA), the negative polarity electric current amount being a product of a time (minutes) during which the tank A polarity is held negative and the electric current value (mA). The restroom odor confirmed includes odor at defecation time and odor adhered to around a toilet, and the garbage odor confirmed includes odor leaked out of the garbage box and odor generated by opening and closing the rid of the garbage box. In confirmation of the restroom odor, the atmospheric temperature was not taken into account for the defecation temperature is constant, while in the garbage odor confirmation, the vicinity of the garbage box was maintained between 18° C.-25° C. In the Test No. 1, the electric current amount of a positive electrolysis electric current in the tank A and the electric current amount of a negative electrolysis current in the tank A are equal to each other, so that the electrolysis in the tank A is equivalent to the diaphragm-free electrolysis, thereby making it impossible to deodorize the restroom odor and the garbage odor due to the PH value of the aqueous solution being 8.2. Based on the results of Test No. 4 to 7, under a condition where the PH value of the tank A is in the vicinity of 4 or less, the restroom odor and the garbage odor can be deodorized and chlorine odor is not distinctively confirmed, however a person feels discomfort in throat, bronchus and lung after staying for a long time in a room. The PH value is desirably from 5 to 8, and more preferably from 6.5 to 7.8. And the PH value is desirably from 6.8 to 7.8 in constant presence of people. The electric current value ratio or the electric current amount ratio for obtaining a proper PH value by repeatedly reversing an electric current direction varies depending on a water quality, a metal ion quantity, a carbonate ion quantity and the like of a sewage water to or the like be used in the deodorization and sterilization apparatus. Therefore, the electric current value ratio or the electric current amount ratio should be appropriately set in accordance with a condition under which the deodorization and sterilization apparatus is used.

Figure 3:
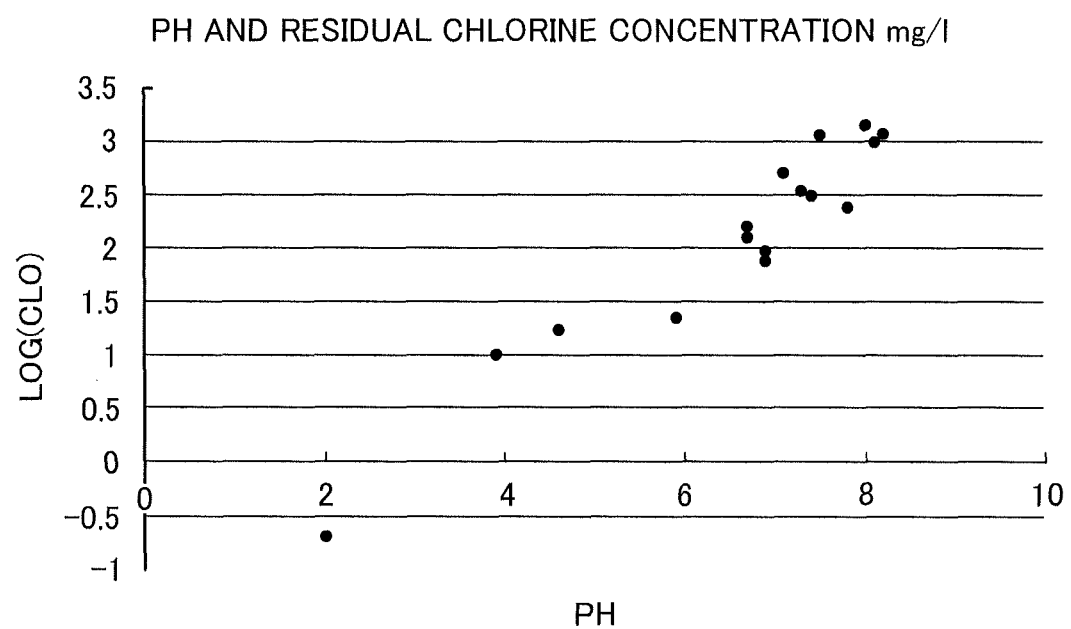
FIG. 3 is a view showing a relationship between a PH value and hypochlorous acid concentration of a liquid generated by the deodorization and sterilization apparatus according to the first and the second embodiments of the present invention.

FIG. 3 shows a graph in which the PH value and the concentration of residual chlorine are extracted and plotted from the Table 1 and Table 2 obtained in the experiments using the apparatuses in the first and the second embodiment and other experiments results. The concentration of the residual chlorine exponentially increases with the increase of alkalinity in the aqueous solution. The graph shown in FIG. 3 shows a correlation between a logarithm of the concentration of the residual chlorine and the PH value of the aqueous solution with some variance. The variance is caused by various factors, such as for example, a gas-liquid interface area of the tank, the electric current value, a water quantity, the salt path, a speed of air flow, a temperature and a time for equilibrium and the like. The deodorization and sterilization apparatus is desirably operated under a condition wherein the residual chlorine concentration is 1,000 mg/l or less, as it is generally known that the residual chlorine concentration being too high can promote a formation of chloric acid. In FIG. 3, CLO denotes the residual chlorine concentration in unit of mg/l.

Figure 4:
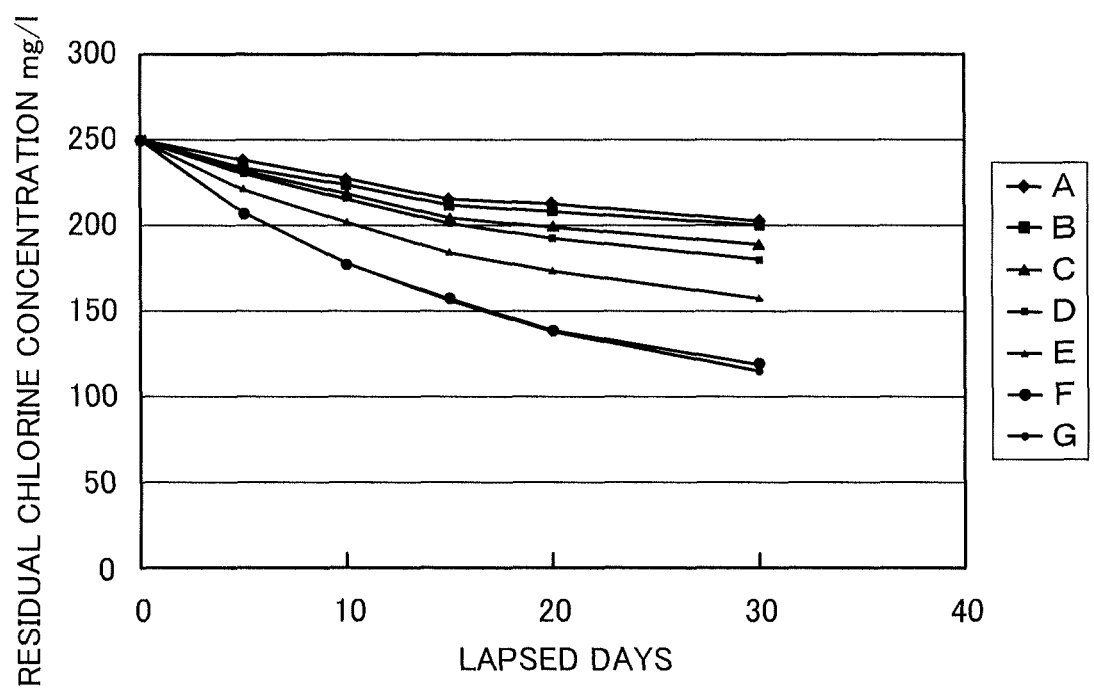
FIG. 4 is a view showing a relationship between a variation of the hypochlorous acid concentration of the hypochlorous acid solution in vessels each of which has a differing lid opening ratio and elapsed days.
Figure 5:
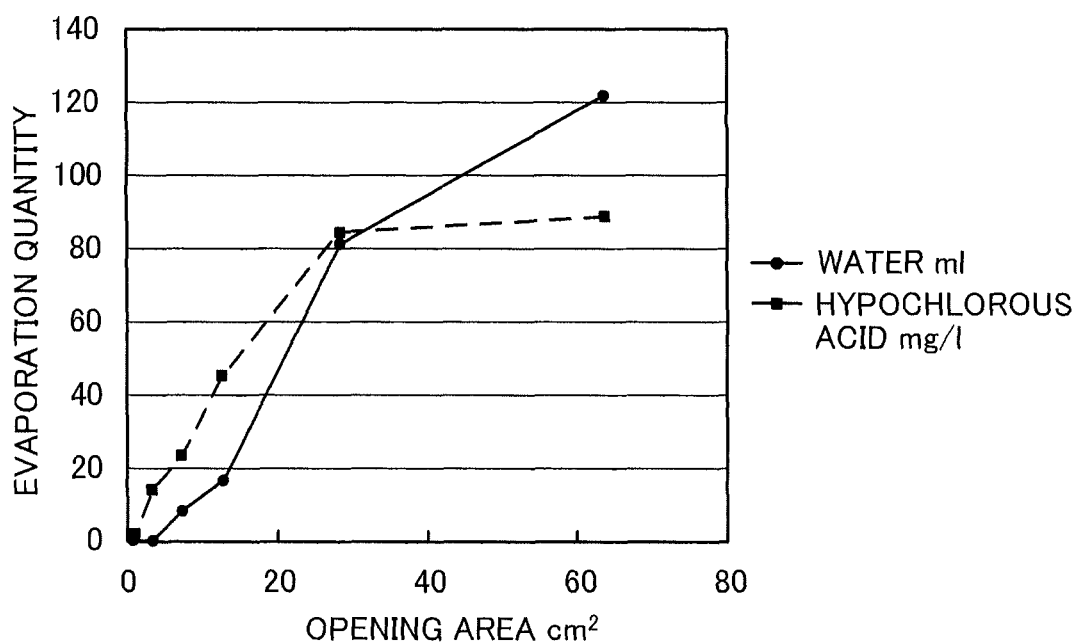
FIG. 5 is a view showing a relationship between an opening portion area and an evaporation quantity of water and hypochlorous acid of the hypochlorous acid solution in vessels of which has the differing lid opening ratio.

FIG. 4 and FIG. 5 show results of experiments, wherein the hypochlorous acid solution having a PH value of 7.1 and the hypochlorous acid concentration of 250 mg/l was filled to the height of 11 cm (891 ml) in each of seven polyester vessels respectively with a depth of 9 cm, a width of 9 cm and a height of 12 cm having a circular opening of 9 cm in diameter at an upper surface of the vessel. At the upper surface of the vessels were respectively placed with polyester plates: a plate A with a circular opening of 0 cm in diameter (no opening), a plate B with a circular opening of 1 cm diameter (0.785 $cm^2$ opening area), a plate C with a circular opening of 2 cm diameter (3.14 $cm^2$ opening area), a plate D with a circular opening of 3 cm diameter (7.07 $cm^2$ opening area), a plate E with a circular opening of 4 cm in diameter (12.56 $cm^2$ opening area), a plate F with a circular opening of 6 cm diameter (28.26 $cm^2$ opening area) and a plate G with a circular opening of 9 cm diameter (63.6 $cm^2$ opening area). The residual chlorine concentration and a residual water quantity were measured with lapsed days per each of the seven vessels which were left in a room of 18-24° C. temperature with no flow of air. FIG. 4 shows a relationship between the residual chlorine concentration and the lapsed days. In FIG. 4, A denotes a vessel with 0 $cm^2$ opening area, B denotes a vessel with 0.785 $cm^2$ opening area, C denotes a vessel with 3.14 $cm^2$ opening area, D denotes a vessel with 7.07 $cm^2$ opening area, E denotes a vessel with 12.56 $cm^2$ opening area, F denotes a vessel with 28.56 $cm^2$ opening area and G denotes a vessel with 63.6 $cm^2$ opening area. FIG. 4 teaches that a reduction of the hypochlorous acid is mainly due to the evaporation of the hypochlorous acid solution in the vessel E, F and G wherein the opening area of the vessel with an opening is 20% or more of the gas-liquid interface area (reduction of the residual chlorine concentration of the vessels E, F and G are twice the reduction of the residual chlorine concentration of the vessel A). FIG. 5 shows a relationship of evaporation amount of the hypochlorous acid and evaporation quantity of water with respect to the opening area of the vessel. The evaporation amount of the hypochlorous acid was calculated on assumptions that the reduction of the residual chlorine in the vessel A is due to decomposition and that a quantity of the reduction of the residual chlorine in vessels B, C, D, E F and G subtracted with the amount of reduction of the residual chlorine in the vessel A is mainly ascribable to the evaporation alone. The evaporation amount of the hypochlorous acid is saturated where the opening area of the vessel is about 30% of the gas-liquid interface area. In the deodorization and sterilization apparatus according to the present invention, power supply and chlorine ion are sufficient, however, the electrolysis of the hypochlorous acid may be disabled due to the reduction of the hypochlorous acid solution. Accordingly, it is essential to suppress the evaporation of water to the minimum in the deodorization and sterilization apparatus according to the present invention. FIG. 5 teaches that the opening area of the vessel is desirably 20%-30% of the gas-liquid interface area, so that the evaporation amount of the hypochlorous acid is secured and the water evaporation amount is suppressed.

Continuous use of the deodorization and sterilization apparatus enhances alkalinity of the aqueous solution in the tank B. However, carbon dioxide in the atmosphere is absorbed into the aqueous solution through the opening of the tank B, so that the aqueous solution in the tank B is neutralized, thereby preventing the deodorization and sterilization apparatus from becoming as harmful as damaging human skin. The alkalinity of the tank B can be neutralized by a small amount of the carbon dioxide in the atmosphere, so that a small clearance for ventilation is sufficient as the opening of the tank B, even though the opening of the tank B may be larger than such a clearance. By the construction as explained above, the deodorization and sterilization apparatus to generate the hypochlorous acid can be easily obtained by connecting with a direct constant current device, a direct constant voltage device or a battery. Further, use of a deliquescent aqueous chloride salt solution, such as for example a high-concentration calcium chloride, as an aqueous chloride salt solution of the deodorization and sterilization apparatus enables the deodorization and sterilization apparatus to absorb water from the atmosphere, thereby making it possible to use the deodorization and sterilization apparatus for a long period without supplementing water. Although the description of the embodiments has been directed to the deodorization use, the deodorization and sterilization apparatus according to the present invention is not limited to the deodorization use, but is applicable to any use where oxidizability of the hypochlorous acid can be utilized such as for example sterilization and the like.

Next, results of sterilization experiments using the Test Apparatus T4 used in the Test No. 13 as shown in Table 1 and will be described hereinafter. Two boxes respectively with a width of 40 cm, a depth of 40 cm and a height of 25 cm were put in a space preserved within a temperature range of 28-32° C. Each of the two boxes was provided therein with a schale containing 25 ml of whole milk and a cup containing 100 ml of the whole milk. One of the two boxes was further provided therein with the test apparatus T4. Thereafter, a corrosion progress of the whole milk was observed. A cover of each of the two boxes was respectively formed with an opening of about 10% in area of the cover. Table 3 shows the corrosion progress status of the whole milk. In one box not provided therein with the test apparatus T4 that generates the hypochlorous acid, the whole milk started to be condensed 48 hours after start of the experiment, and the whole milk was separated into two layers and emitted a corrosion odor 72 hours after the start of the experiment. The experiment was continued until five days after the start of the experiment when there was a strong corrosion odor. On the other hand, in the other box provided therein with the test apparatus T4 that generates the hypochlorous acid, the condensed milk emitted no corrosion odor and had a membrane on a surface 48 hours after the start of the experiment, and thereafter the membrane grew thicker and a yellow tint of the whole milk developed as the lapse of days. Five days after the start of the experiment, there was an odor similar to a butyric acid odor. Seven days after the start of the experiment, the odor was slightly increased and the milk was gelated. Thereafter, the milk was solidified with a progress of water evaporation, thereby weakening the odor. Ten days after the start of the experiment, the solidified milk was crushed and stirred in purified water. The PH value of a supernatant formed as a result of crushing and stirring the solidified milk in the purified water was 4.9. The experiment results explained above indicate that the corrosion of the milk was largely suppressed by existence of the hypochlorous acid generated by the test apparatus T4, particularly growth of alcohol, aldehyde and sulfide producing bacterium in an early phase of the corrosion were suppressed.

TABLE 3

| T4 apparatus Provided/Not Provided | | Lapsed Days | | | | | | |
|---|---|---|---|---|---|---|---|---|
| | | 1 Day | 2 Days | 3 Days | 4 Days | 5 Days | 7 Days | 10 Days |
| With T4 apparatus | Schale Liquid Quantity 15 ml | No Odor | No Odor | No Odor Water evaporated Milk solidified. | No Odor | Slight Butyric Acid Odor (*) | Slight Butyric Acid Odor (*) | Extremely Slight Butyric Acid Odor (*) |
| | Cup Liquid Quantity 100 ml | No Odor | No Odor Membrane on milk surface. | No Odor Membrane on milk surface. | No Odor Membrane on milk surface. | Slight Butyric Acid Odor (*) Yellow tint developed on milk surface. | Butyric Acid Odor (*) Yellow tint developed on milk surface. No water evaporation/ flow | Butyric Acid Odor (*) weakened. Yellow tint developed on milk surface. PH 4.9 Water Evaporated. Milk |
| Without T4 apparatus | Schale Liquid Quantity 15 ml | No Odor | No Odor Milk Slightly Condensed | Putrid Odor Water evaporated. Milk solidified. | Strong Putrid Odor Milk solidified. | Extremely Strong Putrid Odor. Test Terminated. Milk solidified. | | |
| | Cup Liquid Quantity 100 ml | No Odor | No Odor Milk Slightly Condensed | Putrid Odor Milk Condensed. | Strong Putrid Odor Milk Condensed. | Extremely Strong Putrid Odor. Test Terminated Milk Condensed. | | |

Butyric Acid Odor (*): Odor mainly from butyric acid. Similar to cheese odor. Less stimulus than a case not provided with the T4 apparatus.

The deodorization and sterilization apparatus according to the present invention is compact in size and simple in structure, so that the deodorization and sterilization apparatus according to the present invention can be easily mass-produced and consequently can be provided in a low cost. The deodorization and sterilization apparatus according to the present invention is adapted to generate a quantity of the hypochlorous acid sufficient for deodorization for a long period of time and to continuously evaporate the hypochlorous acid through the opening, thereby making it possible to be utilized in deodorization and sterilization of a narrow space, such as for example a restroom, around a garbage box, a dirty utility room in a nursing home and the like.

EXPLANATION OF REFERENCE NUMERALS

A, B ... tank, 11 ... negative electrode lead cable, 12 ... positive electrode lead cable, 13 ... negative electrode lead cable, 21 ... negative electrode, 22 ... positive electrode, 23 ... negative electrode, 3 ... salt path, 4 ... hollow member, 41 ... hollow member inner upper space, 5 ... gas transparent member, 6 ... partition plate

The invention claimed is:

1. A deodorization and sterilization apparatus that electrolyzes an aqueous chloride salt solution filled in a vessel to generate a hypochlorous acid, the deodorization and sterilization apparatus comprising:
    a tank A having an opening formed therein and having a negative electrode and a positive electrode provided therein, the opening communicating with an outside air;
    a tank B having an opening or a clearance formed therein and having a negative electrode provided therein, the opening or the clearance communicating with an outside air;
    a salt path that electrically connects the aqueous chloride salt solution in the tank A and the aqueous chloride salt solution in the tank B with each other;
    a direct current power unit that electrifies the positive electrode and the negative electrode; and
    a control unit that controls a ratio of an electric current value or an electric current quantity of an electric current in the negative electrode in the tank A and an electric current in the negative electrode in the tank B.

2. A deodorization and sterilization apparatus that electrolyzes an aqueous chloride salt solution filled in a vessel to generate a hypochlorous acid, the deodorization and sterilization apparatus comprising:
    a tank A having an opening formed therein and having a positive electrode provided therein and optionally having a negative electrode provided therein, the opening communicating with an outside air;
    a tank B having an opening or a clearance formed therein and having a negative electrode provided therein, and optionally having a positive electrode provided therein, the opening or the clearance communicating with an outside air;
    a salt path that electrically connects the aqueous chloride salt solution in the tank A and the aqueous chloride salt solution in the tank B with each other;
    a direct current power unit that electrifies the positive electrode and the negative electrode; and
    a reverse and control unit that reverses a polarity of the electrode in the tank A and a polarity of the electrode in the tank B and controls a ratio of positive-reverse electrified time or a ratio of positive-reverse electric current quantity.

3. The deodorization and sterilization apparatus as set forth in claim 1, in which the salt path is constituted by a retention material or a salt bridge, the retention material being a material that retains the aqueous chloride salt solution by a nonwoven textile fabric or a felt-like suction material.

4. The deodorization and sterilization apparatus as set forth in claim 1, in which the positive electrode and optionally the negative electrode are accommodated in a hollow member having openings respectively in an upper portion and a lower portion thereof, the upper portion of the hollow member being communicated with the outside air through a gas transparent member which has a gas transparency.

5. The deodorization and sterilization apparatus as set forth in claim 4, in which the gas transparent member is constituted by a gas transparent material or a clearance forming member that forms a clearance between the clearance forming member and the hollow member.

6. The deodorization and sterilization apparatus as set forth in claim 2, in which the salt path is constituted by a retention material or a salt bridge, the retention material being a material that retains the aqueous chloride salt solution by a nonwoven textile fabric or a felt-like suction material.

7. The deodorization and sterilization apparatus as set forth in claim 2, in which the positive electrode and optionally the negative electrode are accommodated in a hollow member having openings respectively in an upper portion and a lower portion thereof, the upper portion of the hollow member being communicated with the outside air through a gas transparent member which has a gas transparency.

8. The deodorization and sterilization apparatus as set forth in claim 7, in which the gas transparent member is constituted by a gas transparent material or a clearance forming member that forms a clearance between the clearance forming member and the hollow member.

\* \* \* \* \*